(12) United States Patent
Thornes et al.

(10) Patent No.: US 11,259,854 B2
(45) Date of Patent: Mar. 1, 2022

(54) ORTHOPAEDIC DEVICE

(71) Applicant: SOTA ORTHOPAEDICS LIMITED, Santry (IE)

(72) Inventors: Brian Thornes, Sutton (IE); Ross McDonald, Howth (IE)

(73) Assignee: SOTA ORTHOPAEDICS LIMITED, Dublin (IE)

( * ) Notice: Subject to any disclaimer, the term of this patent is extended or adjusted under 35 U.S.C. 154(b) by 193 days.

(21) Appl. No.: 16/325,059

(22) PCT Filed: Aug. 11, 2017

(86) PCT No.: PCT/EP2017/070522
§ 371 (c)(1),
(2) Date: Feb. 12, 2019

(87) PCT Pub. No.: WO2018/029374
PCT Pub. Date: Feb. 15, 2018

(65) Prior Publication Data
US 2020/0046413 A1 Feb. 13, 2020

(30) Foreign Application Priority Data
Aug. 12, 2016 (EP) .................................. 16184091

(51) Int. Cl.
*A61B 17/84* (2006.01)
*A61B 17/86* (2006.01)
(Continued)

(52) U.S. Cl.
CPC .......... *A61B 17/844* (2013.01); *A61B 17/863* (2013.01); *A61B 17/7233* (2013.01);
(Continued)

(58) Field of Classification Search
CPC ............ A61B 17/7055; A61B 17/7064; A61B 17/844; A61B 17/7275; A61B 17/742;
(Continued)

(56) References Cited

U.S. PATENT DOCUMENTS

2009/0099610 A1* 4/2009 Johnson ............. A61B 17/7055
606/86 R
2010/0145396 A1* 6/2010 Thornes ............... A61B 17/746
606/313
(Continued)

FOREIGN PATENT DOCUMENTS

| WO | WO1998051228 | 11/1998 |
| WO | WO2009004603 | 1/2009 |

OTHER PUBLICATIONS

International Search Report for PCT/EP2017/070522 dated Nov. 15, 2017.

*Primary Examiner* — Marcela I. Shirsat
(74) *Attorney, Agent, or Firm* — Hueschen and Sage

(57) ABSTRACT

This invention relates to a coupling for an orthopaedic device. Also disclosed in an orthopaedic device comprising a coupling of the invention and method for the use of the orthopaedic device. The orthopaedic device finds utility as a bolt apparatus for fixation of bones such as fractures of the femur, although it may be used in any suitable bone.

6 Claims, 5 Drawing Sheets

(51) Int. Cl.
*A61B 17/74* (2006.01)
*A61B 17/00* (2006.01)
*A61B 17/72* (2006.01)
*A61B 17/56* (2006.01)

(52) U.S. Cl.
CPC ....... *A61B 17/7258* (2013.01); *A61B 17/7266* (2013.01); *A61B 17/7275* (2013.01); *A61B 17/742* (2013.01); *A61B 17/8685* (2013.01); *A61B 2017/00477* (2013.01); *A61B 2017/00862* (2013.01); *A61B 2017/564* (2013.01); *A61B 2017/8655* (2013.01)

(58) Field of Classification Search
CPC ... A61B 17/863; A61B 17/68; A61B 17/7233; A61B 17/7258; A61B 17/7266; A61B 17/8625; A61B 17/8685; A61B 2017/564; A61B 2017/00477; A61B 2017/8655
USPC .... 606/310, 63, 313, 314, 315, 316; 411/16, 411/45, 53, 60.2, 32, 39
See application file for complete search history.

(56) References Cited

U.S. PATENT DOCUMENTS

2012/0184993 A1* 7/2012 Arambula .......... A61B 17/7064
606/246
2014/0257484 A1 9/2014 Flower \* cited by examiner

ORTHOPAEDIC DEVICE

FIELD OF THE INVENTION

This invention relates to a coupling for an orthopaedic device. Also disclosed in an orthopaedic device comprising a coupling of the invention and method for the use of the orthopaedic device. The orthopaedic device finds utility as a bolt apparatus for fixation of bones such as fractures of the femur, although it may be used in any suitable bone.

BACKGROUND TO THE INVENTION

Bone fixation devices are well known and they find particular utility in the field of orthopaedic surgery, where they are used to fix a bone, which has sustained a fracture, across a fracture site. Generally, the type of fracture determines the type of surgery.

Patients with femoral neck fractures are treated with pinning or hip arthroplasty, depending on the age of the patient and the presence and degree of displacement. Patients with intertrochanteric fractures are treated with a sliding hip screw or an intramedullary hip screw, depending on the stability and location of the fracture.

If the fracture is stable, a sliding hip screw coupled to a side plate that is screwed onto the femoral shaft is used. The screw provides proximal fragment fixation. It is set inside a telescoping barrel that allows impaction of the bone, which promotes fracture union. A lateral buttress must be intact to stop excessive sliding of the screw.

When the direction of a fracture is parallel to the femoral neck, the fracture can be extremely unstable. This fracture type is called the reverse oblique pattern. A high rate of failure occurs if the fracture is treated with a sliding hip screw and a side plate. Because of the angle of the fracture, there is no bone laterally to stop the screw from sliding.

For unstable intertrochanteric fractures, including those of the reverse oblique pattern and those with subtrochanteric extension, an intramedullary hip screw is often indicated. This device combines a sliding hip screw with an intramedullary nail. Intramedullary hip screws can be placed through small incisions, and blood loss may be less than with a hip screw and side plate. The nail acts as a metal buttress to prevent sliding and provides better fixation in unstable fracture patterns.

Failure mechanisms of a hip screw include non-union, screw cut-out, nail breakage, malunion, and limp. Although sliding of the hip screw allows for bone compression and hopefully healing, it shortens the limb and causes abduction weakness. Most complications are subsequently treated with total hip arthroplasty.

SUMMARY OF THE INVENTION

According to a first aspect of the present invention there is provided a coupling for an orthopaedic device, the coupling comprising an annular body having an internal threaded surface comprising at least two sections, wherein the threads of a first section are in reverse orientation to the threads of a second or subsequent section.

Optionally, the at least two sections are contiguous sections. Optionally, the at least two sections are spaced apart sections. Further optionally, the at least two sections are spaced apart, contiguous sections.

Optionally, the annular body has at least one open end. Further optionally, the annular body has two open ends. Still further optionally, the annular body has two opposing open ends.

Optionally, the annular body is a substantially cylindrical annular body. Further optionally, the annular body is a substantially cylindrical annular body having at least one open end. Still further optionally, the annular body is a substantially cylindrical annular body having two open ends. Still further optionally, the annular body is a substantially cylindrical annular body having two opposing open ends.

Optionally, the annular body is a substantially circular cylindrical annular body. Further optionally, the annular body is a substantially circular cylindrical annular body having at least one open end. Still further optionally, the annular body is a substantially circular cylindrical annular body having two open ends. Still further optionally, the annular body is a substantially circular cylindrical annular body having two opposing open ends.

Optionally, an inner surface of the annular body is shaped and dimensioned to engage with the threaded shaft of an orthopaedic device. Further optionally, an inner surface of the annular body is shaped and dimensioned to reversibly engage with the threaded shaft of an orthopaedic device.

Optionally, at least one of the at least two sections of the annular body is shaped and dimensioned to engage with at least part of the threaded shaft of an orthopaedic device. Further optionally, at least one of the at least two sections of the annular body is shaped and dimensioned to engage with at least part of the threaded shaft of an orthopaedic device.

Optionally, each of the at least two sections of the annular body is shaped and dimensioned to engage with the threaded shaft of an orthopaedic device, wherein the orthopaedic device may be the same or a different orthopaedic device. Further optionally, at least each of the at least two sections of the annular body is shaped and dimensioned to engage with the threaded shaft of an orthopaedic device, wherein the orthopaedic device may be the same or a different orthopaedic device.

According to a second aspect of the present invention there is provided an orthopaedic device comprising a threaded shaft comprising at least two portions, wherein the threads of a first portion are in reverse orientation to the threads of a second or subsequent portion; and a coupling according to a first aspect of the present invention.

Optionally, the at least two portions of the threaded shaft are contiguous portions. Optionally, the at least two portions of the threaded shaft are spaced apart portions. Further optionally, the at least two portions of the threaded shaft are spaced apart contiguous portions.

Optionally, the orthopaedic device further comprises an expandable section operable between a contracted position and an expanded position.

Optionally, the orthopaedic device comprises an expandable section operable between a contracted position and an expanded position; a threaded shaft comprising at least two portions, wherein the threads of a first portion are in reverse orientation to the threads of a second or subsequent portion; and a coupling according to a first aspect of the present invention.

Optionally, the orthopaedic device further comprises at least two bodies mountable to the threaded shaft.

Optionally, the orthopaedic device comprises an expandable section operable between a contracted position and an expanded position; a threaded shaft comprising at least two portions, wherein the threads of a first portion are in reverse orientation to the threads of a second or subsequent portion; at least two bodies mountable to the threaded shaft; and a coupling according to a first aspect of the present invention.

Optionally, at least one of the at least two mountable bodies comprises the coupling according to a first aspect of the present invention.

Optionally, the orthopaedic device comprises an expandable section operable between a contracted position and an expanded position; a threaded shaft comprising at least two portions, wherein the threads of a first portion are in reverse orientation to the threads of a second or subsequent portion; two bodies mountable to the threaded shaft; wherein one of the two mountable bodies is a coupling according to a first aspect of the present invention.

Optionally, the orthopaedic device comprises an expandable section operable between a contracted position and an expanded position; a threaded shaft comprising at least two portions, wherein the threads of a first portion are in reverse orientation to the threads of a second or subsequent portion; two bodies mountable to the threaded shaft; wherein one of the two mountable bodies is a coupling comprising an annular body having an internal threaded surface comprising at least two sections, wherein the threads of a first section are in reverse orientation to the threads of a second or subsequent section.

Optionally, the orthopaedic device comprises an expandable section operable between a contracted position and an expanded position; a threaded shaft comprising two portions, wherein the threads of a first portion are in reverse orientation to the threads of a second portion; two bodies mountable to the threaded shaft; wherein one of the two mountable bodies is a coupling comprising an annular body having an internal threaded surface comprising two sections, wherein the threads of a first section are in reverse orientation to the threads of a second section.

Optionally, the threads of the first section of the annular body are shaped and dimensioned to engage with the threads of the second portion of the threaded shaft of the orthopaedic device. Further optionally, the threads of the first section of the annular body are shaped and dimensioned to reversibly engage with the threads of the second portion of the threaded shaft of the orthopaedic device.

Optionally, the threads of the first section of the annular body are oriented to engage with the threads of the second portion of the threaded shaft of the orthopaedic device. Further optionally, the threads of the first section of the annular body are oriented to reversibly engage with the threads of the second portion of the threaded shaft of the orthopaedic device.

Optionally, each or any of the mountable bodies are in operable association with the expandable section, to displace the expandable section between the contracted position and the expanded position by applying force to the respective ends of the expandable section, such that each of the respective ends of the expandable section are advanced toward the opposing respective end.

Further optionally, each or any of the mountable bodies is in operable association with the expandable section, to displace the expandable section between the contracted position and the expanded position by simultaneously applying force to the respective ends of the expandable section, such that each of the respective ends of the expandable section are independently advanced toward the opposing respective end. Each respective end is displaced by the application of a force to each of the respective ends of the expandable section. Each respective end can be optionally simultaneously displaced by the independent and simultaneous application of a force to each of the respective ends of the expandable section.

Optionally, each or any of the mountable bodies is arranged for displacement in response to rotation of the threaded shaft to apply mechanical pressure to the respective ends of the expandable section.

Optionally, the threaded shaft has first and second portions. Further optionally, the threaded shaft has first and second portions, wherein the threads of the first portion are in reverse orientation to the threads of the second portion.

Optionally, the first body is mountable to the first portion of the threaded shaft and the second body is mountable to the second portion of the threaded shaft.

Optionally, the first and second portions are located adjacent respective opposing ends of the threaded shaft.

Optionally, at least one end of the threaded shaft is dimensioned and arranged to provide means for rotating the threaded shaft. Further optionally, at least one end of the threaded shaft is dimensioned and arranged to provide means for delivering torque to the threaded shaft. Still further optionally, at least one end of the threaded shaft is dimensioned and arranged to receive a torque delivery device such as a screwdriver, hex key, or similar device.

Optionally, each or any of the at least two bodies is engagable with at least one of the respective ends of the expandable section. Further optionally, each or any of the at least two bodies is irreversibly engagable with at least one of the respective ends of the expandable section.

Optionally, the expandable section is reversibly expandable. Further optionally, the section is reversibly expandable under mechanical pressure.

Optionally, the expandable section is collapsible along its longitudinal axis. Further optionally, the expandable section is radially inwardly collapsible.

Optionally, the expandable section comprises at least two expandable members that extend from the longitudinal axis of the apparatus under mechanical pressure. Further optionally, the expandable members extend radially from the longitudinal axis of the apparatus under mechanical pressure.

Optionally, each of the expandable members comprises a deformable arm. Optionally, at least one point of folding is provided along each deformable arm.

Optionally, each or any of the points of folding comprises a point of weakness, a hinge mechanism, or any such mechanism that will facilitate the folding of the deformable arm at a desired location.

Optionally, at least one of the at least two mountable bodies defines a portion of the expandable section. Further optionally, at least one of the at least two mountable bodies comprises a screw thread located on a portion of the expandable section. Still further optionally, at least one of the at least two mountable bodies comprises a screw thread located on at least part of the inner surface of the expandable section.

Optionally, the coupling and/or the orthopaedic device is formed of a material that is suitable for sterilisation, so as to be provided in a sterile packaged state for use. Optionally, the material is autoclavable. Optionally, the material is surgical stainless steel.

According to a third aspect of the present invention, there is provided a method for fixation of bones, the method comprising the steps of reducing the fracture; providing a channel across the fracture; inserting an orthopaedic device according to a second aspect of the invention in the channel; and fixing the orthopaedic device in the channel.

Optionally, the fixing step comprises displacing the expandable section toward the expanded position by applying force to the respective ends of the expandable section, such that each of the respective ends of the expandable section are advanced toward the opposing respective end.

Optionally, the fixing step comprises rotating the threaded shaft.

Optionally, the method comprises the additional step of coupling the orthopaedic device.

BRIEF DESCRIPTION OF THE DRAWINGS

Embodiments of the invention will now be described, by way of non-limiting example, with reference to the accompanying drawings, in which.

DETAILED DESCRIPTION OF THE INVENTION

Figure 1A:
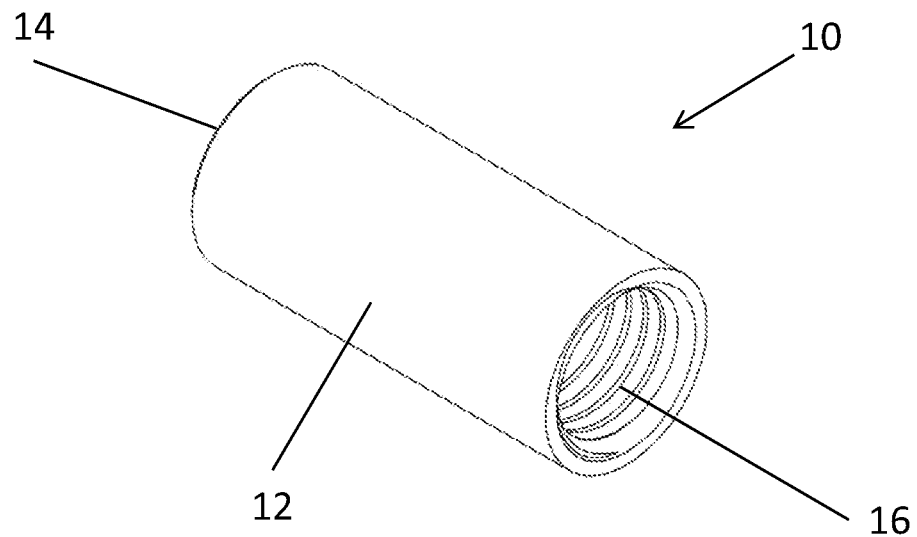
FIG. 1A is a perspective view of a coupling according to a first aspect of the present invention.
Figure 1B:
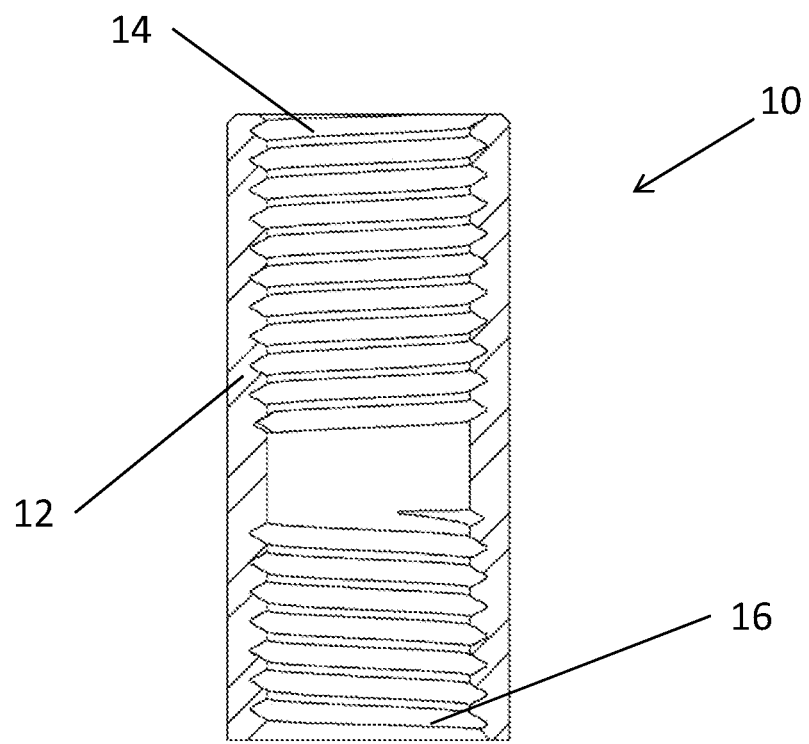
FIG. 1B is a sectional view of the coupling of FIG. 1A.

Referring now to FIGS. 1A and 1B of the drawings, there is shown a coupling 10 according to a first aspect of the invention. The coupling 10 comprises an annular body 12, which can be a substantially cylindrical shape having two opposing open ends, but can be of any cross-sectional shape. For example, the annular body 12 can be a substantially non-circular cylindrical shape to inhibit rotation of the annular body 12 relative to the external environment in which it is in contact, when in use.

The annular body 12 has an internal threaded surface comprising two sections 14, 16. The threaded sections 14, 16 are each helically threaded sections. The threads of the first section 14 are in reverse orientation to the threads of a second section 16. The two sections 14, 16 are spaced apart contiguous sections having a non-threaded section therebetween. The annular body 12 has opposing open ends, each shaped and dimensioned to receive a complimentary threaded shaft.

The inner surface of the annular body 12 is shaped and dimensioned to engage with the threaded shaft of an orthopaedic device. In specific embodiments, at least one of the at least two sections 14, 16 of the annular body 12 is shaped and dimensioned to engage with the threaded shaft of an orthopaedic device. In certain embodiments, each of the at least two sections 14, 16 of the annular body 12 is shaped and dimensioned to engage with the threaded shaft of an orthopaedic device. The orthopaedic device may be the same or a different orthopaedic device. For example, a first section 14 can be shaped and dimensioned to engage with the threaded shaft of an orthopaedic device as described herein and a second section 16 can be shaped and dimensioned to engage with the threaded shaft of a different orthopaedic device. In such a case, the threaded shaft of each different orthopaedic device can be a different threaded shaft, and the two sections 14, 16 of the annular body 12 can be differentially shaped and dimensioned to engage with the respective threaded shaft of each orthopaedic device.

Figure 2:
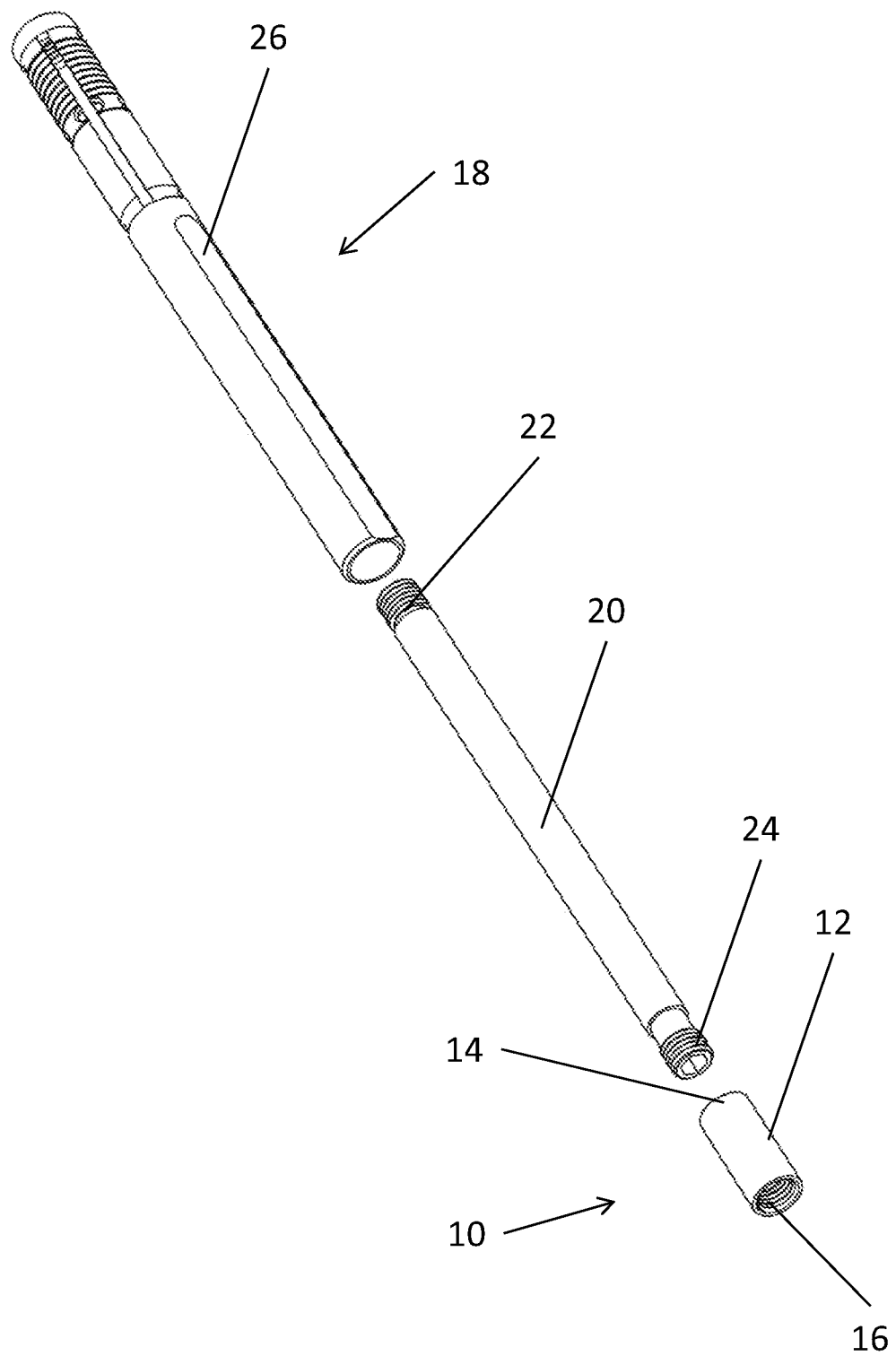
FIG. 2 is an exploded perspective view of an orthopaedic device according to a second aspect of the present invention.
Figure 3:
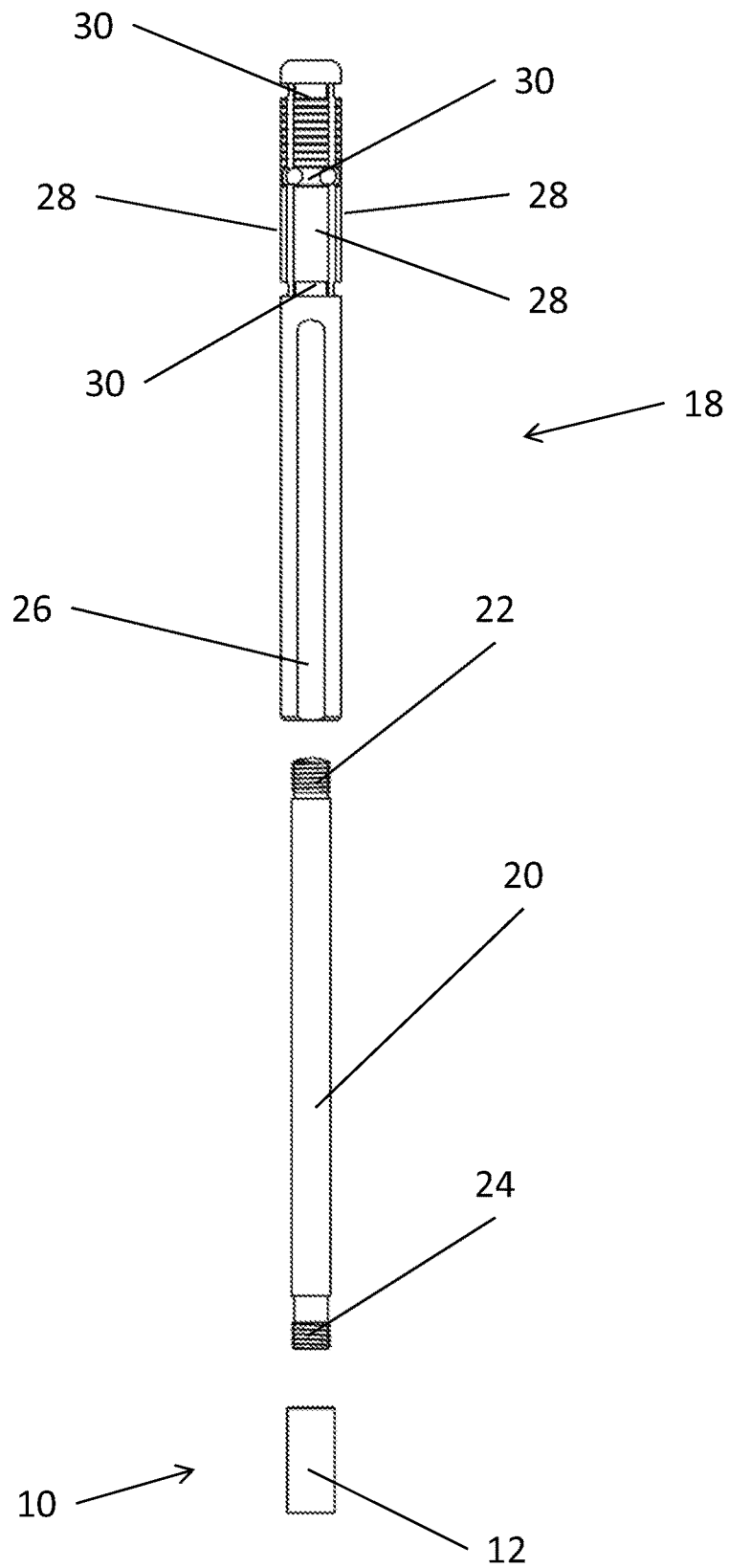
FIG. 3 is a plan view of the orthopaedic device of FIG. 2.
Figure 4:
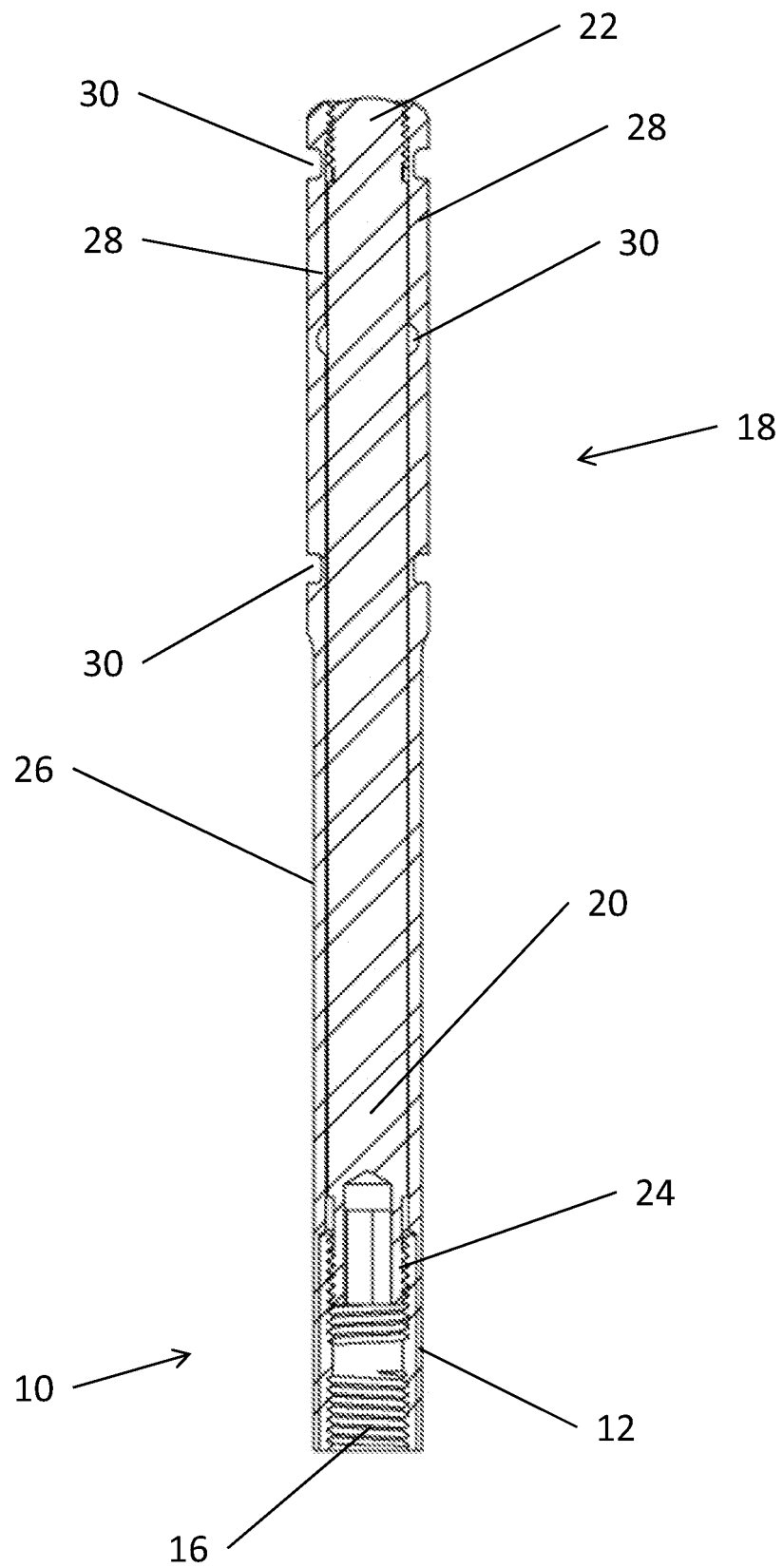
FIG. 4 is a sectional view of the orthopaedic device of FIG. 2 in an assembled contracted position.
Figure 5:
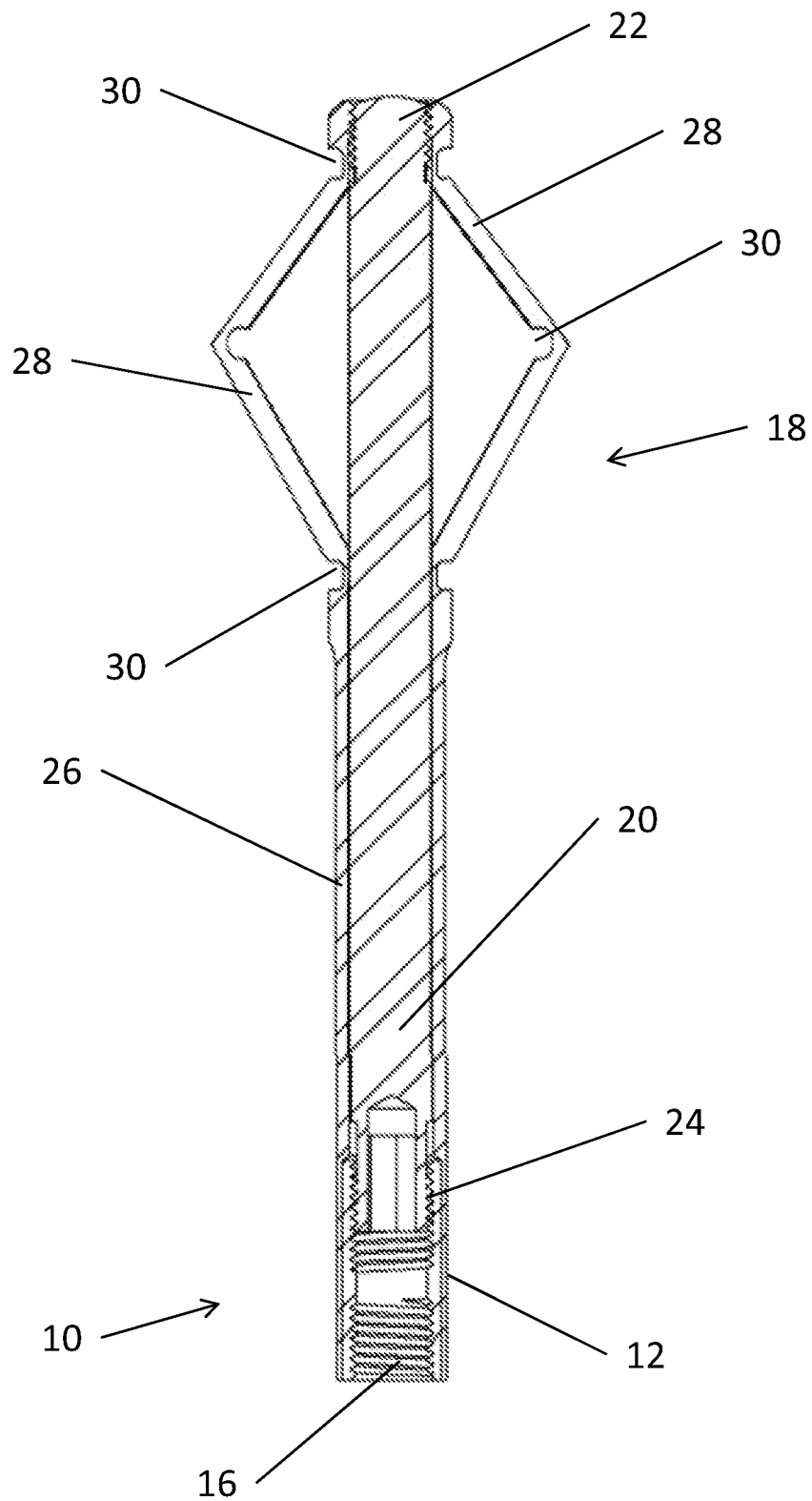
FIG. 5 is a sectional view of the orthopaedic device of FIG. 2 in an assembled expanded position.

Referring to FIG. 2, there is shown an orthopaedic device 18 according to a second aspect of the invention. The orthopaedic device 18 comprises a threaded shaft 20 comprising at least two portions 22, 24; a coupling 10; and an expandable section 26 operable between a contracted position and an expanded position.

The present invention finds utility as a bolt apparatus for fixation of bones such as fractures of the femur, although it may be used in any suitable bone.

The threaded shaft 20 comprises an elongate member, which is generally cylindrical in shape. Two distinct helical screw threaded portions 22, 24 are provided adjacent the terminal ends of the threaded shaft 20. The relative orientation of each screw thread 22, 24 is opposite in direction to that of the other. The first and second portions 22, 24 of the threaded shaft 20 are spaced apart contiguous portions; and the threads of a first portion 22 are in reverse orientation to the threads of the second portion 24. The first and second portions 22, 24 are located adjacent respective opposing ends of the threaded shaft 20.

One end of the threaded shaft 20 is dimensioned and arranged to provide means for rotating the threaded shaft 20, for example by providing means for delivering torque to the threaded shaft. The end of the threaded shaft 20 can be dimensioned and arranged to receive a torque delivery device such as a screwdriver, hex key, or similar device. A hexagonal socket (not shown) can be provided at the proximal end of the threaded shaft 20, and can be shaped and adapted to receive a hex key or similar torque delivery device.

The orthopaedic device 18 further comprises two bodies mountable to the threaded shaft 20. Two mountable bodies are provided, each of which can be generally cylindrical in shape and open at both ends. Each respective mountable body can be of similar form, but has a helical screw thread that is oriented in the opposite direction relative to the other. The first body is mountable to the first portion 22 of the threaded shaft 20 and the second body is mountable to the second portion 24 of the threaded shaft 20.

A helical screw thread can be provided on the inner surface of each mountable body. The internal diameter of the body is generally of similar length to the external diameter of the threaded shaft 20, whereby the screw thread of each mountable body can engage with the respective screw threaded portions 22, 24 of the threaded shaft 20.

Each of the mountable bodies is in operable association with the expandable section 26, to displace the expandable section 26 between the contracted position and the expanded position by applying force to the respective ends of the expandable section 26, such that each of the respective ends of the expandable section 26 are advanced toward the opposing respective end. Each of the mountable bodies displaces the expandable section 26 between the contracted position and the expanded position by simultaneously applying force to the respective ends of the expandable section 26.

As used herein, the term "advanced" is intended to mean the positive displacement of an object between a first position and a second position, wherein the first and second positions are different, spaced-apart positions. It is understood that, in this aspect of the present invention, the first position of each respective end is the position when the expandable section 26 is in the fully expanded position, and the second position of each respective end is the position when the expandable section 26 is in the fully contracted position. Each respective end is displaced by the application of a force to each of the respective ends of the expandable section 26. Each respective end can optionally be simultaneously displaced by the simultaneous application of a force to each of the respective ends of the expandable section 26.

Each of the two bodies is engagable with the respective end of the expandable section 26. Each of the mountable bodies is in operable association with the expandable section 26, to displace the expandable section 26 between the contracted position and the expanded position by applying force to the respective ends of the expandable section 26, such that each of the respective ends of the expandable section 26 are independently advanced toward the opposing respective end.

As used herein, the term "independently advanced" is intended to mean the positive and independent displacement of an object between a first position and a second position, wherein the first and second positions are different, spaced-apart positions. Each respective end is displaced by the application of a force to each of the respective ends of the expandable section 26. Each respective end can be displaced by the independent application of a force to each of the respective ends of the expandable section 26.

In specific embodiments, one of two mountable bodies comprises the coupling 10. Each of the mountable bodies is arranged for displacement in response to rotation of the threaded shaft 20 to apply mechanical pressure to the respective ends of the expandable section 26. The coupling 10 can comprise an annular body 12 having an internal threaded surface comprising two sections 14, 16, wherein the threads of the first section 14 are in reverse orientation to the threads of the second section 16. The threads of the first section 14 of the annular body 12 are shaped and dimensioned to engage with the threads of the second portion 24 of the threaded shaft 20 of the orthopaedic device 18.

In certain specific embodiments, one of the two mountable bodies can define a portion of the expandable section 26. The mountable body can be integral with the expandable section 26. The mountable body can comprise a screw thread located on at least part of the inner surface of the expandable section 26.

The expandable section 26 can be reversibly expandable. The expandable section 26 is collapsible along its longitudinal axis, such that the expandable section 26 is radially inwardly collapsible.

The expandable section 26 comprises a generally cylindrically shaped tube, which is open at both ends. At least two generally rectangular apertures are provided on the curved surface of the expandable section 26, each of which extends a limited length along the longitudinal axis of the expandable section 26. The area between the apertures defines deformable arms 28, such that the expandable section 26 comprises a plurality of arms 28 that extend from the longitudinal axis of the orthopaedic device 18 under mechanical pressure. A point of weakness 30 is provided at each of the respective ends of each deformable arm 28, where the deformable arm 28 is attached to the respective ends of the expandable section 26; and adjacent the centre point of the length of each deformable arm 28, such that each arm 28 is a deformable arm having at least one point of folding 30 along each deformable arm 28. Each of the points of folding 30 comprises a point of weakness, a hinge mechanism, or any such mechanism that will facilitate the folding of the deformable arm at a desired location.

The inner surface of the expandable section 26 is generally circular in transverse cross-section. The internal diameter of the expandable section 26 is generally of similar length to the external diameter of the threaded shaft 20, whereby the threaded shaft 20 can be located longitudinally and rotated coaxially within the expandable section 26.

The coupling 10 and/or the orthopaedic device 18 can be formed of a material that is suitable for sterilisation, for example a material that is autoclavable, such as surgical stainless steel.

To assemble the orthopaedic device, the first section 14 of the coupling 10 is engaged with the second screw threaded portion 24 the threaded shaft 20. The threaded shaft 20 is then inserted coaxially into the lumen of the expandable section 26, and the first screw threaded portion 14 of the threaded shaft 20 is engaged with a helical screw thread on the inner surface of the expandable section 26, such that the coupling 10 is located coaxially and conterminally with the lumen of the expandable section 26.

Once assembled, each of the mountable bodies is located on one of the screw threaded portions 22, 24 of the threaded shaft 20. In certain embodiments, one of the mounted bodies is a helical screw thread located on the inner surface of the terminal end of that expandable section 26. In certain embodiments, the other of the mounted bodies is the coupling 10. Each of the mountable bodies is in tandem but opposite orientation relative to the other one, and is located at each respective end of the expandable section 26. Each of the mountable bodies can be attached to each respective end of the expandable section 26 by an adherent means such as an adhesive and/or by compressive tension applied to the expandable section 26.

In use, the threaded shaft 20 is rotated using a hex key or similar torque delivery device, inserted into the hexagonal socket is provided at the proximal end of the threaded shaft 20. Rotation of the threaded shaft 20 within the expandable section 26 causes the terminal end of the expandable section to advance along the first screw threaded portion 22 of the threaded shaft 20; and the coupling 10 to advance, in the opposite direction, along the second screw threaded portion 24 of the threaded shaft 20. This applies mechanical pressure to the respective ends of the expandable section 26, wherein the respective ends are bought sequentially into closer proximity relative to one another, causing the deformable arms 28 to deform at each of the points of weakness 30, and to expand radially from the longitudinal axis of the orthopaedic device 18.

A further orthopaedic device or a set screw, each comprising a threaded shaft, can be engaged with the second section 16 of the coupling 10 to provide a stop, which inhibits further rotation of the threaded shaft 20, therein assuring that the expandable section 26 does not collapse under external pressure from the surrounding bone, with which it is in contact. The second section 16 of the coupling 10 can receive a set screw (not shown), which comprises a generally cylindrically shaped member having a helical screw thread is provided on the outer surface of the set screw. The external diameter of the set screw is generally of similar length to the internal diameter of the second section 16 of the coupling 10, whereby the screw thread on the outer surface of the set screw can engage with the second section 16 of the coupling 10.

Rotation of the threaded shaft 20 in the opposite direction can ultimately cause the deformable arms 28 to retract toward the longitudinal axis of the orthopaedic device, thereby facilitating the removal of the device, if required.

The exposure and overall technique is similar to that used (as standard) for a dynamic hip screw. The conventional technique permits fixation of a wide variety of inter-trochanteric, subtrochanteric and basilar neck fractures using, for example, a dynamic hip screw system provided by Synthes™. Reference may be made to the Technique Guide produced by Synthes™ in this regard. However, an advantage to using the expanding hip bolt will be the possibility of utilising a minimally invasive technique, necessitating specialised instruments, to avoid the need for an open operation.

For the purposes of the present invention, a modified standard technique is described, as an alternative to the conventional technique. The patient is anaesthetised by general, regional or local anaesthesia, and placed supine on a standard fracture table. The leg is manipulated under x-ray fluoroscopy image intensifier to achieve a closed reduction. A longitudinal incision is placed (as in standard technique) on the lateral aspect of the thigh and the lateral part of the proximal femoral shaft is exposed using a combination of sharp and blunt dissection through the adipose tissue, fascia lata and vastus lateralis muscle.

Using a 2 mm guide wire with a 135 degree drill guide, the position for the proximal fixation is obtained. The optimum position for the expanding hip bolt is similar to that of a DHS lag screw, with the tip-apex distance being less than 5 mm on both AP and lateral views with the image intensifier. The hole for the bolt is drilled over the guide wire using a 9.25 mm drill bit. The wider drill-hole for the barrel at the lateral cortex is drilled using a 13 mm drill bit, over the guide wire.

The assembled orthopaedic device 18 can be advanced until in an optimum position, as confirmed using the image intensifier. The deformable arms 28 of the expandable section 26 should not be deployed until the orthopaedic device 18 is in the optimum position. The deformable arms 28 are expanded using a torque hex-screwdriver, which rotates the threaded shaft 20, thus causing the mountable bodies (one of which is the coupling 10) to converge, compressing the expandable section 26. The torque hex-screwdriver has a torque limiter to prevent excessive torque force being applied to the orthopaedic device 18. The progress of the deformable arms 28 expanding radially can be followed using the image intensifier. The screwdriver can be removed once the deformable arms 28 have been deployed to an optimal position, as checked on the image intensifier or as limited by the torque limiter.

Fracture compression if necessary, can be performed by inserting an introducer and delivering controlled traction. Leg traction via the fracture table should be released prior to this manoeuvre. A set screw can be now inserted into the coupling 10 to prevent rotation or telescoping of the threaded shaft 20. Final confirmation of the fixation is checked with the image intensifier, and the wound closed.

The invention claimed is:

1. An orthopaedic device comprising:
 (a) a threaded shaft comprising at least two portions, wherein the threads of a first portion are in reverse orientation to the threads of a second portion;
 (b) an expandable section operable between a contracted position and an expanded position and having respective opposing ends;
 (c) a single coupling comprising an annular body having an internal threaded surface comprising at least two sections, wherein the threads of a first section are in reverse orientation to the threads of a second section, and wherein the first section is shaped and dimensioned to engage with the threads of the second portion of the threaded shaft of the orthopaedic device; and
 (d) a body comprising a screw thread located on a portion of the expandable section and mountable to the first portion of the threaded shaft of the orthopaedic device;
 wherein the coupling and the screw thread are each in operable association with the expandable section, to displace the expandable section between the contracted position and the expanded position by applying force to the respective ends of the expandable section, such that each of the respective ends of the expandable section is advanced toward the opposing respective end.

2. The orthopaedic device according to claim 1, wherein each of the coupling and the screw thread are arranged for displacement in response to rotation of the threaded shaft to apply mechanical pressure to the respective ends of the expandable section.

3. The orthopaedic device according to claim 1, wherein the at least two sections are spaced apart sections.

4. The orthopaedic device according to claim 1, wherein each of the coupling and the screw thread are engageable with at least one of the respective ends of the expandable section.

5. The orthopaedic device according to claim 1, wherein the expandable section comprises at least two expandable members that extend from the longitudinal axis of the apparatus under mechanical pressure.

6. The orthopaedic device according to claim 5, wherein each of the expandable members comprises a deformable arm.

* * * * *